(12) United States Patent
Acharya et al.

(10) Patent No.: US 7,914,824 B2
(45) Date of Patent: Mar. 29, 2011

(54) HERBAL EXTRACT FOR RENAL DISORDERS

(75) Inventors: Vidya Narayan Acharya, Mumbai (IN); Triptikumar Mukhopadhyay, Mumbai (IN); Swati Ajay Piramal, Mumbai (IN)

(73) Assignee: Piramal Life Sciences Limited, Maharashtra (IN)

( * ) Notice: Subject to any disclaimer, the term of this patent is extended or adjusted under 35 U.S.C. 154(b) by 0 days.

(21) Appl. No.: 10/591,023

(22) PCT Filed: Apr. 4, 2005

(86) PCT No.: PCT/IB2005/051103
§ 371 (c)(1),
(2), (4) Date: Jun. 27, 2008

(87) PCT Pub. No.: WO2005/097149
PCT Pub. Date: Oct. 20, 2005

(65) Prior Publication Data
US 2008/0274212 A1    Nov. 6, 2008

Related U.S. Application Data

(60) Provisional application No. 60/561,335, filed on Apr. 9, 2004.

(51) Int. Cl.
*A01N 65/00*    (2009.01)
(52) U.S. Cl. .................................................... 424/725
(58) Field of Classification Search .................. None
See application file for complete search history.

(56) References Cited

U.S. PATENT DOCUMENTS

| | | | |
|---|---|---|---|
| 5,486,160 A | 1/1996 | Rossi et al. | |
| 5,529,778 A | 6/1996 | Rohatgi | |
| 5,886,029 A | 3/1999 | Dhaliwal | |
| 6,136,316 A | 10/2000 | Mehrotra et al. | |
| 6,251,383 B1 * | 6/2001 | Upadhyay et al. | 424/93.1 |
| 6,274,595 B1 | 8/2001 | Young et al. | |
| 2002/0142055 A1 * | 10/2002 | De Souza et al. | 424/762 |
| 2003/0147896 A1 * | 8/2003 | Solanki | 424/181.1 |

FOREIGN PATENT DOCUMENTS

| | | |
|---|---|---|
| IN | 183805 | 10/1998 |
| WO | WO 91/08750 | 6/1991 |
| WO | WO 9108750 * | 6/1991 |
| WO | WO 02/053166 | 7/2002 |

OTHER PUBLICATIONS

International Search Report for International Application No. PCT/IB05/51103 dated Feb. 9, 2006.
Kumar, V. et al. Diuretic Activity of Herbal Nefroliv and Frusemide in Normal Rats. Phytomedica. 2002, vol. 3, pp. 73-75.
Meher, S. K. et al. Nephroprotectivc effect of NEFROLIV (trademark) in Centainicin Induced Nephrotoxieity. Phytomedica. 2001, vol. 2, No. 1-2, pp. 41-47.
Yi'e, U. M. et al. Immunotherapeutic Modification of *Escheriehi coli* Peritonitis and Bacteremia by *Tinospora cordifolia*. Journal of Postgraduate Medicine. 1992, vol. 38, No. 1, pp. 13-15.
Thatte, U. M. et al. Immunotherapeutie modification of experimental infections by Indain Medicinal Plants. Phytotherapy Research. 1989, vol. 3, No. 2, pp. 43-49.
Kullarni et al. Study of the Immunostimulant Activity of Naphthoquinone Extract of Leaves of Lawsonia A Alba Linn. Indian Drugs. 1998 pp. 427-433.

* cited by examiner

*Primary Examiner* — Michael V Meller
(74) *Attorney, Agent, or Firm* — Hamre, Schumann, Mueller & Larson, P.C.

(57) ABSTRACT

The present invention relates to the use of standardized extract of *Tinospora cordifolia* as an immunoadjuvant in the treatment of renal disorders such as nephrotic syndrome and chronic recurrent urinary tract infections, both complicated and uncomplicated.

The present invention also relates to pharmaceutical compositions comprising the standardized extract of *Tinospora cordifolia*.

The present invention further relates to a method of treatment of renal disorders such as recurrent urinary tract infection particularly occurring due to relapsing *E. coli, Klebsiella* and other gram negative infections and to a method of treatment of nephrotic syndrome using standardized extract of *Tinospora cordifolia* as an immunoadjuvant in conjunction with conventional therapy.

6 Claims, No Drawings

HERBAL EXTRACT FOR RENAL DISORDERS

FIELD OF THE INVENTION

The present invention relates to methods and compositions for treating renal disorders. More specifically, the present invention relates to methods and compositions comprising standardized extract of *Tinospora cordifolia* in the treatment of renal disorders such as nephrotic syndrome and chronic recurrent urinary tract infections, both complicated and uncomplicated.

BACKGROUND OF THE INVENTION

Renal disorders form important components of both "lifestyle" and "infective" diseases in humans. Both types of diseases can lead to chronic kidney damage and can progress to end stage renal disease and chronic renal failure. Complicated urinary tract infections and nephrotic syndrome represent the most common and important group of disorders that constitute a major cause of chronic renal failure.

An important renal disease associated with morbidity and progress to end stage renal failure is chronic recurrent urinary tract infection, which can lead to rend scarring going to chronic pyelonephritis. Chronic recurrent urinary tract infection is usually treated by therapy with antibacterial agents. However, the development of increasing antibacterial resistance with each episode plays an important role in non-healing with slow and steady progression to a chronic state due to impaired immunity produced by repeated infections.

Urinary tract infections (UTIs) are one of the most common infectious diseases encountered in the practice of medicine today. UTIs encompass a spectrum of clinical and pathological conditions involving various parts of the urinary tract. The syndromes range from symptomatic bacteriuria to peripheric abscess with sepsis. Each has its own unique epidemiology, natural history and diagnostic considerations. Differentiating syndromes associated with UTI have important implications for treatment and prognosis.

Complicated urinary tract infection refers to urinary infection, which occurs in an individual with functional metabolic or structural abnormalities of the genitourinary tract. These abnormalities promote infection through compromising adequate drainage of urine or by establishing a nidus, from which bacteria cannot be eradicated, as in case of diabetics and in renal failure subjects.

Recurrent infection may be either relapse, where infection recurs with the pro therapy infecting organism and suggests a failure to eradicate the organism from the genitourinary tract, or re-infection, where a new organism establishes infection. In recurrent UTI the impaired host defense and the ability of the bacteria to adhere to the cell walls lining the ureters, play an important role in the recurrences.

*E. coli* is the cause in most of the UTI cases and treatment consists of a course of antibacterials. Other organisms involved are *Klebsiella, Proteus, Enterobacter, Citrobacter, Serratia* and *Pseudomonas*. Synthetic antimicrobial agents of the older members of quinolone class such as nalidixic acid have been available for the treatment of UTI. However, these drugs have limited therapeutic utility and the organisms rapidly develop resistance.

Newer drugs such as fluorinated 4-quinolones like ciprofloxacin, ofloxacin, norfloxacin, lomefloxacin, trimethoprim-sulfamethoxazole and other antibacterial agents like amoxicillin, nitrofurantoin and ampicillin are equally efficacious against UTI. Complicated UTIs normally require a longer course of antibacterial therapy that is associated with the various side effects.

Nephrotic syndrome is a condition marked by very high levels of protein in the urine; low levels of protein in the blood; swelling, especially around the eyes, feet, and hands; and high cholesterol. It leads to hypoalbuminemia, lipiduria, hyperlipidemia, with elevated triglycerides and other lipids, and edema.

Nephrotic syndrome can occur with many diseases, including the kidney diseases caused by primary glomerulonephritis, systemic diseases like diabetes mellitus and vasculitis etc., but some causes are unknown. Prevention of nephrotic syndrome relies on controlling these diseases and preventing relapses by use of anti-proteinuric agents including use of steroids and other immunosuppressive agents.

Immunosuppressive agents are often used with frequently relapsing nephrotic syndrome for steroid-sparing effects. Drugs like cyclophosphamide and chlorambucid were initially shown to be effective in prolonging remission but their potential side effects such as carcinogenesis and infertility have limited their use.

Hence there is a need to analyze the present treatment of renal disorders and to develop new effective drug therapies that are devoid of side effects for the above renal diseases.

*Tinospora cordifolia* also known in India as Guduchi/amruta is one of the Rasayanas which has been designated as "Ekadravya Rasayana" in the ancient Indian system of medicine [Ayurveda] i.e. to be used as a single entity for its pro-host immunostimulant activity and has been called "the Nectar of life". This is one of the plant products that has been extensively studied as an immunostimulant by well-known practitioners of modern allopathic medicine.

Numerous polyherbal classical and proprietary formulations having *Tinospora cordifolia* as one of the ingredients, are available in the Indian market as well as for export. Also, products such as ADBAC™ and IMMUMOD™ having *Tinospora cordifolia* as a single herb component as a natural immunostimulant are commercially available in India. These products claim to contain an aqueous extract of *Tinospora cordifolia*.

Extensive experimental and clinical work has shown the immune enhancing effects of *Tinospora cordifolia*. This has been established to be mediated through stimulation of macrophage activity which in turn leads to increased secretion of granulocyte-monocyte colony stimulating factor (GM-CSF).

PCT patent application WO 9108750 describes the use of parts of the natural plant *Tinospora cordifolia* for the treatment of cancerous disease.

U.S. Pat. No. 5,529,778 describes a polyherbal composition containing *Tinospora cordifolia* as one of the constituents for the prophylaxis and treatment of influenza, tuberculosis infection, AIDS, and other immunodeficient conditions. However, the role or advantage of *Tinospora cordifolia* in the composition is not reported in the patent.

U.S. Pat. No. 6,136,316 describes a polyherbal composition with *Tinospora cordifolia* as one of the ingredients for treating acute Hepatitis E and Hepatitis B.

U.S. Pat. No. 5,886,029 discloses a composition of epicatechin and gymnemic acid with *Tinospora* for the treatment of diabetes. Indian patent no. 183805 describes a process for the preparation of immunomodulator from *Tinospora* and claims polysaccharide as an active principle.

PCT application WO02053166 discloses a formulation comprising a standard herbal extract of *Tinospora cordifolia* as an immunomodulating agent, a method for the standardization of extract of *Tinospora cordifolia*, and a method of treatment of a health condition associated with the modulation of immunity such as osteomyelitis, cancer, breast cancer, diabetes, respiratory tract infection, tonsilitis, chronic bronchitis, otitis media, tuberculosis, hepatitis, AIDS, burns, pediatric disease.

Though voluminous data are available on the use of *Tinospora cordifolia* in various diseases, there is no indication in the published literature regarding the use of *Tinospora cordifolia* as an immunoadjuvant in the treatment of renal disorders such as chronic recurrent urinary tract infections; both complicated and uncomplicated, and nephrotic syndrome.

SUMMARY OF THE INVENTION

The present invention is directed to a method of treatment of renal disorders such as chronic recurrent urinary tract infections; both complicated and uncomplicated, and nephrotic syndrome comprising administration of the pharmaceutical composition containing standardized extract of *Tinospora cordifolia*.

The above summary of the present invention is not intended to describe each discussed embodiment of the present invention. This is the purpose of the detailed description that follows.

DETAILED DESCRIPTION OF THE INVENTION

Complicated urinary tract infections and nephrotic syndrome represent the most common and important group of disorders that constitute a major cause of chronic renal failure.

Urinary infection in the setting of functional or structural abnormalities of the urinary tract will not be treated effectively unless the underlying abnormality promoting the infection is corrected; it reflects that individuals with complicated UTIs tend to have recurrent infection and multiple intervention. Prior anti-bacterial therapy and the potential for nosocomial acquisition of micro-organisms both increase the likelihood of more resistant microorganisms emerging in subsequent infections.

It has been observed that recurrent infection is the norm for individuals with complicated UTIs where the underlying genitourinary abnormality cannot be corrected; or metabolic abnormality can be controlled; but cannot be cured. The symptoms of infection often subside before the bacteria causing the infection are completely eliminated, hence requiring a long-term treatment regimen.

In the case of recurrent UTIs, conventional anti-bacterial therapy means the use of anti-bacterial agents selected from trimethoprim, trimethoprim-sulfamethoxazole combination, ampicillin, cephalothin, nitrofurantoin, gentamicin and fluoroquinolones (e.g. ciprofloxacin, norfloxacin). In the case of nephrotic syndrome, conventional steroid therapy means the use of prednisolone and methyl prednisolone.

High levels of protein in the urine indicate the condition of nephrotic syndrome, which is a major cause of chronic renal failure resulting from damage to the kidneys' glomeruli. Glomeruli enclose tiny blood vessels that filter waste and excess water from the blood and send them to the bladder as urine.

Nephrotic syndrome is characterized by massive proteinuria due to the damage caused to the glomerular basement membrane, the main filtering unit of the kidneys. The damage is mainly associated with inflammation resulting from either primary immune involvement of the kidney or secondary involvement due to immune mediated systemic disorders.

Nephrotic syndrome occurs due to a variety of kidney diseases caused by primary glomerulonephritis like Membranoproliferative Glomerulonephritis/Mesangiocapillary Glomerulonephritis (MPGN), Focal segmental glomerulosclerosis (FSGS), Focalproliferative Glomerulonephritis (FPGN) and Minimal change nephrotic syndrome (MCNS). They could be immune complex mediated or cellular immune responses.

Nephrotic syndrome patients may achieve remission once the underlying cause, if known, has been treated. Eighty percent of nephrotic syndrome cases that are caused by minimal-change disease can be treated successfully with steroids such as prednisone. However, nephrotic syndrome in which certain types of glomerular diseases, such as those characterized by immune complex are the underlying cause, can not be cured easily. In these cases, the kidneys may gradually lose their ability to filter wastes and excess water from the blood. If kidney failure occurs, the patient will need dialysis or a kidney transplant.

Most steroids have potential side-effects such as weight gain, fluid retention and raised blood pressure, headache, elevation of blood sugar levels, arterial and venous thrombosis, in some patients thinning of bones osteoporosis, thinning of skin and easy bruising, and risk of serious infections like peritonitis, systemic sepsis pneumonia, cellulitis and UTI. Steroids can cause patients to become steroid dependent and to develop steroid toxicity, frequent infections and other complications.

The present inventors have developed an immunoadjuvant therapy for the treatment of renal diseases such as chronic recurrent urinary tract infection and nephrotic syndrome.

In an embodiment, the present invention relates to the novel use of the standardized extract of *Tinospora cordifolia* as an immunoadjuvant in the treatment of renal disorders such as nephrotic syndrome and chronic recurrent urinary tract infections; both complicated and uncomplicated.

In another embodiment, the invention relates to method of treatment of renal disorders such as recurrent urinary tract infection occurring due to relapsing *E. coli, Klebsiella, Proteus, Enterobacter, Citrobacter, Serratia* and *Pseudomonas* infection by providing effective immunoadjuvant therapy, in conjunction to conventional antibacterial therapy.

In an embodiment, the invention provides an effective immunoadjuvant therapy, in conjunction to conventional steroid therapy for the treatment and prevention of relapses of nephrotic syndrome.

In another embodiment, the invention relates to method of treatment of renal disorders such as nephrotic syndrome occurring due to a variety of kidney diseases caused by primary glomerulonephritis like Membranoproliferative Glomerulonephritis/Mesangiocapillary Glomerulonephritis (MPGN), Focal segmental glomerulosclerosis (FSGS), Focalproliferative Glomerulonephritis (FPGN) and Minimal change nephrotic syndrome (MCNS).

In another embodiment, the invention provides a pharmaceutical composition comprising standardized extract of *Tinospora cordifolia* along with other pharmaceutical carriers.

In an embodiment, the invention provides a pharmaceutical composition comprising standardized extract of *Tinospora cordifolia* in combination with at least one other herbal constituent.

In another embodiment of the invention is directed to a method of making a composition useful for treating renal disorders by mixing the *Tinospora cordifolia* extract with a carrier or diluent.

While not intending to be bound by theory, the immune enhancing effects of *Tinospora cordifolia* are believed to be mediated through stimulation of macrophage activity leading to increased secretion of granulocyte-monocyte colony stimulating factor [GM-CSF]. As a result, increases in IL2 and IFN-gamma result in increased natural killer cell activity, ultimately leading to an anti-inflammatory effect.

*Tinospora cordifolia* can be obtained commercially. By way of example, *Tinospora cordifolia* can be obtained commercially from Kisalaya Herbals Limited, Indore, India. *Tinospora cordifolia* extract can also be prepared. By way of example, one process for the preparation of an extract of *Tinospora cordifolia* comprises the following steps: 1) powdering dried stems of *Tinospora cordifolia* followed by treating it with water, 2) extracting it with hot water, 3) filtering the extract obtained in step 2, 4) partly concentrating the filtrate under vacuum, and 5) spray drying the material obtained in step 4 to get the extract as fine powder.

*Tinospora cordifolia* extract can be standardized by the technique of phagocytosis measurement using polymorphonuclear leukocytes (PMNL) that evaluates the immunomodulatory potential of the extract (Indian drugs, 1998, 35(7), 427-433). The bioactivity of the extract is measured by determining the percentage of phagocytosis using PMNL leukocytes over a base value as described in the example. All active extracts of *Tinospora cordifolia* have a percentage phagocytosis of not less than 30% over a base value.

The composition comprising standardized extract of *Tinospora cordifolia* can be mixed with pharmaceutically acceptable carriers and formulated into therapeutic dosage forms such as tablets, capsules, liquid orals, nasal sprays, creams, sterile injectable preparations, suppositories, etc. The composition can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, or vehicles. The extract of *Tinospora cordifolia*, as it is in the composition, may be a liquid, a powder, etc.

As used herein, the term pharmaceutically acceptable carrier means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cotton seed oil, safflower oil, sesame oil, olive oil, corn oil, and soybean oil; glycols, such as propylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium laryl sulfate and magnesium stearate, as well as coloring agents, releasing agents, coating agents, sweetening, flavoring and perfuming agents; preservatives and antioxidants can also be present in the composition, according to the judgment of the formulator.

The composition of the invention may be prepared by mixing the various components of the composition using conventional methods. The preferred composition of the invention may be prepared according to the constituent ranges set forth herein in Table 2.

In an embodiment, the dose of the standardized extract varies between 20-80 mg/kg body wt per day. In a particular embodiment, the dose varies between 20-25 mg/kg body wt. administered in equal portions twice a day or thrice a day. In a further embodiment, in children, the dose varies between 25-30 mg/kg body wt. administered in equal portions twice a day or thrice a day. In an embodiment, total dose of the standardized extract varies between 400 mg-4000 mg per day.

In an embodiment, the standardized extract is administered to patients suffering from UTI for a period of one month to 3 months continuously, and intermittently up to 18 months. In an embodiment, the standardized extract is administered to patients for nephrotic syndrome for a period from 4-6 weeks up to 12 months continuously or intermittently. The period of administration of the standardized extract may vary depending on intensity of disease and response of the patient.

In an exemplary embodiment, a composition of standardized extract of *Tinospora cordifolia* extract was prepared in the form of a capsule to study the effect of the herbal extract of *Tinospora cordifolia* as an immunoadjuvant in patients in the treatment of chronic recurrent urinary tract infection, nephrotic syndrome and other renal disorders.

During clinical studies it has been observed that, in a group of patients with chronic UTI under the treatment of anti bacterial like Lomefloxacin, Trimethoprim, Sulphamethoxazole, Ciprofloxacin and the like, the colony count in urine culture was more than about $10^5$. After the treatment with the pharmaceutical composition comprising *Tinospora cordifolia* there is either no growth, or count in urine culture is less than about $10^3$.

This indicates that the treatment of cases having recurrent urinary tract infection with proven episodes on more than about 20 occasions over a period of more than about 15 months, with a pharmaceutical composition comprising herbal extract of *Tinospora cordifolia* stops any further episode of urinary tract infection and urine culture may become negative in the future. This indicates that a pharmaceutical composition comprising standardized extract of *Tinospora cordifolia* may act on the root cause of the relapse of urinary tract infection by eliminating the organism from the system.

For nephrotic syndrome the efficacy of pharmaceutical composition comprising standardized extract of *Tinospora cordifolia* was evaluated in patients suffering from primary nephrotic syndrome. The patient's age ranges between about 5 to about 70 years.

The following examples are merely intended to illustrate the present invention in further detail but should by no means be construed as limiting the scope of the invention.

EXAMPLE 1

Standardization Assay of *Tinospora cordifolia*

The *Tinospora cordifolia* extract was obtained from Kisalaya Herbals Limited, Indore, India. The extract was a brown colored, free flowing fine powder which was bitter in taste. The extract was characterized by analytical tests such as Bulk density (tapped), pH, alcohol soluble extractives and water soluble extractives. The results obtained were: bulk density (tapped): 0.55-0.65/ml; pH. (1% w/v in Water): 5-6.8; alcohol soluble extractives: 8-15% w/w on dried basis; and water soluble extractives: not less than 95% w/w on dried basis.

Human blood (2-3 drops) was collected on a sterilized glass slide. The slide was kept on the cotton bed in the sterilized petri-dish. It was then incubated at 37° C. for 25 minutes, the clot was removed and the slide was washed with saline (0.9% aq. NaCl solution). The presence of PNLs (polymorphonuclear leukocytes) was confirmed by observing the slide under a microscope. PMNLs were then incubated with different concentrations of the *Tinospora cordifolia* extract or a control at 37° C. for 35-40 min.

After 40 minutes the slide was drained, then flooded with culture of *Candida albicans* and incubated at 37° C. for 1 h.

The slide was then washed with water, fixed with methanol, stained with a Giemsa stain and observed under an oil immersion microscope. The mean number of phagocytosed cells on the slide was determined for 100 granulocytes using morphological criteria.

Percentage phagocytosis was calculated for both control and *Tinospora cordifolia* and is shown in Table 1 below:

TABLE 1

| Percentage of Phagocytosis | |
|---|---|
| Control | 14.33% |
| *Tinospora cordifolia* (0.5 mg/ml) | 25.33% |
| *Tinospora cordifolia* (1 mg/ml) | 40.00% |

Percentage phagocytosis values are indicative of the activity level of the immune system. A greater percentage phagocytosis demonstrates enhanced activity of the immune system. Therefore, the data indicates that *Tinospora cordifolia* activates the immune system more than the control.

EXAMPLE 2

Composition with Standardized Extract of *Tinospora cordifolia*

A standardized extract of *Tinospora cordifolia* was combined with colloidal silicon dioxide and magnesium stearate to form a composition with the amounts listed below in Table 2. The composition was then made into the form of a capsule.

TABLE 2

| Contents of Each Capsule: | |
|---|---|
| Ingredients | mg/capsule |
| Standardized extract of *Tinospora cordifolia* | 500.0 |
| Colloidal silicon dioxide | 1.0 |
| Magnesium stearate | 3.0 |
| Total fill weight | 504.0 |

EXAMPLE 3

Effect of *Tinospora cordifolia* as an Immunoadjuvant in Patients with Recurrent Urinary Tract Infection The *Tinospora cordifolia* composition of Example 2 was administered orally to patients with recurrent urinary tract infection. Patients were divided into 2 groups. Group I consisted of patients, young males, and females who continued to have recurrent infections over a period of three months in spite of adequate antibacterial therapy and in whom no underlying cause, such as anatomical or physiological [e.g., pregnancy related] aberrations, was found. Group II consisted of patients of middle and older age groups who had chronic recurrent urinary tract infection that continued beyond 3 months and up to 18 months, in spite of the fact that remediable causes like obstruction or underlying G.U. Tuberculosis had long been corrected.

The Group I subjects consisted of 0.4 patients who received the *Tinospora cordifolia* composition in the dosage of 20-25 mg/kg body wt. for one month, about 10 days before and 20 days after starting appropriate anti-bacterial agent such as Lomefloxacin, Trimethoprim, Sulphamethoxazole, and Ciprofloxacin. Duration of administration of *Tinospora cordifolia* may be reduced to 20-24 days depending on urine—routine, culture, and anti-bacterial sensitivity test results.

The subjects in Group II were administered the *Tinospora cordifolia* composition in the same dosage; but given for longer period of time of 3 months. One patient from Group II was given 2 courses of *Tinospora cordifolia* spread over a nine-month period. He had recurrent UTI with proven episodes based on urine culture on 21 occasions over a period of 18 months before administering *Tinospora cordifolia*.

Colony count from urine culture was calculated before and after the administration of *Tinospora cordifolia*. The results are shown in Table 3 below.

TABLE 3

| | Colony Count |
|---|---|
| Treatment with antibacterial agent | $10^5$ |
| Treatment with antibacterial agent in conjunction with *Tinospora cordifolia* | $<10^3$ or no growth |

In addition, all treated patients had a complete resolution over a one year observation period with no further episodes of UTI and urine culture becoming negative and remaining so over the period of observation.

EXAMPLE 4

Effect of *Tinospora cordifolia* as an Immunoadjuvant in Patients with Nephrotic Syndrome Efficacy of *Tinospora cordifolia* was evaluated in double-blind randomized placebo-controlled parallel group study in patients with primary nephrotic syndrome. Patients were divided into two groups of 20 patients of age group 5 years to 60 years. Patients of the first group received steroids such as prednisolone or methyl prednisolone and placebo where as patients of the second group were treated with the said steroids and *Tinospora cordifolia*. The *Tinospora cordifolia* composition of Example 2 was administered orally in the dosage of 25-35 mg/kg body weight in divided doses for a period of 12 months as an adjuvant therapy to the steroids.

Urine samples were examined for repeat routine urine analysis, spot urine protein/creatinine ratio after regular time intervals. Haematocrit, proteinuria ratio, WBC (total and differential), BUN, serum creatinine, bilirubin, SGOT, SGPT, alkaline phosphatase, serum proteins including albumin and globulin, serum lipid and cholesterol were investigated.

Efficacy of *Tinospora cordifolia* was evaluated on the basis of clinical and biochemical criteria such as time to response, duration of remission, relapse rate and observations in relapsed cases. Proteinuria and protein/creatinine ratio were obtained pre-treatment, during the treatment and post-treatment.

The results of clinical and biochemical studies indicate the improvements: the infective episodes of all types were reduced, thereby reducing the relapses in many cases. The results obtained with patients of the second group are: the side effects of the steroids like acne; buffalo hump (under the chin), striae and other side effects of the steroids were minimized to a considerable extent.

EXAMPLE 5

Effect of *Tinospora cordifolia* as an Immunoadjuvant in Patients with Primary Nephrotic Syndrome Efficacy of *Tinospora cordifolia* was evaluated in randomized placebo-controlled parallel group study in patients with primary nephrotic syndrome caused by Membranoproliferative Glomerulonephritis/Mesangiocapillary Glomerulonephritis (MPGN), Focal segmental glomerulosclerosis (FSGS), Focalproliferative Glomerulonephritis (FPGN) and Minimal change nephrotic syndrome (MCNS).

Patients were divided into two groups of 5 patients each of age group 5 years to 30 years. Patients of the first group (5 patients) received prednisolone orally in dosage 60 mg/m$^2$ of body surface area or 1 mg/kg body weight depending on age, and placebo, whereas patients of the second group (4 patients) were treated with prednisolone and *Tinospora cordifolia*. The *Tinospora cordifolia* composition of Example 2 was administered orally in the dosage of 20-30 mg/kg body weight in two or three divided doses for a period of 12 months as an adjuvant therapy to steroids.

Urine samples were examined at base line and on follow up as per fixed protocol for repeat routine urine analysis, spot urine protein/creatinine ratio after regular time intervals. Haemoglobin, Haematocrit, proteinuria ratio, WBC (total and differential), BUN, serum creatinine, bilirubin, SGOT, SGPT, alkaline phosphatase, serum proteins including albumin and globulin, serum lipid and cholesterol were investigated in a similar pattern.

Efficacy of *Tinospora cordifolia* was evaluated on the basis of clinical and biochemical criteria such as time to response, duration of remission, relapse rate, observations in relapsed cases and side effects of steroid therapy including infections. Proteinuria and protein/creatinine ratio were obtained pre-treatment, during the treatment and post-treatment.

The steroids are given in dosage 60 mg/m$^2$ of body surface area or 1 mg/kg body weight depending on age, for 1 month. After one month steroid dose is slowly reduced on the basis of clinical and biochemical criteria in both the groups. The results of clinical and biochemical studies are as shown in Tables 4a, 4b, 5a and 5b. Follow up is completed with the 9 cases (no follow up with case no. 5 and case no. 7). Time of remission and number of relapses were calculated on the basis of urine protein/creatinine ratio.

The results obtained with patients of the first group are: time of remission is much longer, variable degree of steroid side effects, infective episodes and poor response in spite of steroid therapy. In some cases, patients shoved good initial response. However, they had severe relapse with several severe side effects.

Tables 4a and 4b show that, there was no response from case no. 2 and 8. In case no. 2 there was some initial response. However, at 6.5 months developed a severe relapse with severe steroid side effects. Case no 8 also shows good initial response at 1 month, developed a relapse with several side effects at 3.5 months. The other 3 cases—1, 3 and 4—also show variable degree of steroid side effects and poor response in spite of therapy.

The results obtained with patients of the second group are: remission achieved in 12 months follow up. *Tinospora cordifolia* reduces the rate and severity of relapse and these relapses respond on continuing the *Tinospora cordifolia* with whatever dose of steroid is being given. In most of the cases there were no steroidal side effects like cushingoid, acne, buffalo hump (under the chin) and striae.

Tables 5a and 5b indicate that 4 cases on *Tinospora cordifolia* i.e., case nos. 6, 9, 10 and 11 have achieved remission in 12 months follow up. These results are very significant especially in cases 6, 10 and 11 in view of the fact that the types of glomerular disease that they suffered from were FPGN, MPGN and FSGS. It has been observed that in case no. 6, at the end of 6 months follow up, there was a relapse on reduction of dose of steroid. However, on continuation of the same steroid dose together with *Tinospora cordifolia* as the added drug, remission was achieved at the end of 12 months. This result is also significant as this was a case of MPGN which otherwise is very difficult to treat.

TABLE 4a

Steroid side effects and infective episodes in first group patients (Placebo therapy)

| Case no. | Age | Indication | Steroid side effects ||||  No. of infective episodes |
| --- | --- | --- | --- | --- | --- | --- | --- |
| | | | Cushingoid | Acne | Buffalo hump | Striae | |
| 1 | 19 | MPGN | Yes | Yes | Yes | No | None |
| 2 | 10 | MPGN | Yes | Yes | Yes | No | 2 |
| 3 | 7 | MPGN | Yes | Yes | No | No | None |
| 4 | 10 | FSGS | Yes | Yes | Yes | No | None |
| 8 | 13 | MCNS | Yes | No | Yes | No | None |

TABLE 4b

Time of remission and relapse in first group patients (Placebo therapy)

| Case no. | Observations | Day 0 | Day 8 | 1 month | 3.5 month | 6.5 month | 10 month | 12 month | No. of relapse | Time of Remission |
| --- | --- | --- | --- | --- | --- | --- | --- | --- | --- | --- |
| 1 | U | 3 | 2 | 2 | 3 | 3 | 3 | 4 | No response to steroid | — |
|   | S | 2.1 | 2.3 | 3.1 | 2.1 | 2.4 | 2.3 | 2.3 | | |
|   | P/C | 4:1 | 3:1 | 2.3:1 | 4.3:1 | 3.2:1 | 3.7:1 | 3.7:1 | | |
| 2 | U | 3 | 2 | 0 | ab | 4 | Lost to follow up || 1 | 4 weeks |
|   | S | 1.7 | 2.7 | 3.8 | 3 | 1.8 | | | | |
|   | P/C | 5.2:1 | 2.5:1 | 0.06:1 | 0.04:1 | 5.8:1 | | | | |

TABLE 4b-continued

Time of remission and relapse in first group patients (Placebo therapy)

| Case no. | Observations | Day 0 | Day 8 | 1 month | 3.5 month | 6.5 month | 10 month | 12 month | No. of relapse | Time of Remission |
|---|---|---|---|---|---|---|---|---|---|---|
| 3 | U | 3 | 3 | 2 | ab | ab | ab | 3 | 1 | 10 weeks |
|   | S | 2 | 1.8 | 2.7 | 3.9 | 3.2 | 3.3 | 2 | | |
|   | P/C | 3.6:1 | 2.4:1 | 1.5:1 | 0.1:1 | 0.06:1 | 0.05:1 | 3.1:1 | | |
| 4 | U | 3 | ab | ab | ab | ab | 3 | ab | 1 | 3 weeks |
|   | S | 1.8 | 2.8 | 4.2 | 3.6 | 3.2 | 2.4 | 2 | | |
|   | P/C | 1.7:1 | 0.22:1 | 0.07:1 | 0.06:1 | 0.3:1 | 2.9:1 | 0.3:1 | | |
| 8 | U | 4 | ab | ab | 4 | Lost to follow up | | | 1 | 4 weeks |
|   | S | 2.3 | 3.8 | 3.8 | 2 | | | | | |
|   | P/C | 1.3:1 | 0.5:1 | 0.09:1 | 1.8:1 | | | | | |

U: Urine Protein;
S: Serum Albumin;
P/C: Urine Protein/Creatinine ratio;
ab: absent TABLE 5a Steroid side effects and infective episodes in second group patients (Drug therapy)

| | | | Steroid side effects | | | | No. of infective |
| Case no. | Age | Indication | Cushingoid | Acne | Buffalo hump | Striae | episodes |
|---|---|---|---|---|---|---|---|
| 6 | 27 | FPGN | Yes | Yes | Yes | Yes | None |
| 9 | 10 | MCNS | Yes | No | No | No | None |
| 10 | 8 | MPGN | No | No | No | No | None |
| 11 | 13 | FSGS | No | No | No | No | 1 |

TABLE 5b

Time of remission and relapse in second group patients (Drug therapy)

| Case no. | Observations | Day 0 | Day 8 | 1 month | 3.5 month | 6.5 month | 10 month | 12 month | No. of relapse | Time of Remission |
|---|---|---|---|---|---|---|---|---|---|---|
| 6 | U | 4 | Tr | ab | Tr | 4 | 1 | ab | 1 | 2 weeks |
|   | S | 2 | 2.4 | 4 | 4 | 2.3 | 3 | 4.3 | | |
|   | P/C | 5.8:1 | 0.08:1 | 0.01:1 | 0.01:1 | 3.5:1 | 0.8:1 | 0.04:1 | | |
| 9 | U | 3 | ab | ab | Ab | 1 | ab | ab | 1 | 2 weeks |
|   | S | 2 | 2.4 | 3.4 | 4.1 | 3.3 | 2.3 | 3.8 | | |
|   | P/C | 2.2:1 | 0.4:1 | 0.2:1 | 0.02:1 | 0.7:1 | 0.4:1 | 0.04:1 | | |
| 10 | U | 2 | Tr | — | ab | ab | ab | ab | No | 2 weeks |
|    | S | 2.6 | 3.9 | — | 3.8 | 3.9 | 3.9 | 3.9 | | |
|    | P/C | 2.6:1 | 0.04:1 | — | 0.03:1 | 0.03:1 | 0.02:1 | 0.04:1 | | |
| 11 | U | 4 | 4 | 4 | 3 | 3 | 3 | 1 | No | 6.5 months |
|    | S | 1.9 | 2 | 2.6 | 2.8 | 3.5 | 3.5 | 3.9 | | |
|    | P/C | 9.8:1 | 9:1 | 3.7:1 | 2.1:1 | 0.9:1 | 0.9:1 | 0.5:1 | | |

U: Urine Protein;
S: Serum Albumin;
P/C: Urine Protein/Creatinine ratio;
ab: absent;
Tr: -Trace The results indicate that nephrotic syndrome which occurs due to primary glomerulonephritis with varying histological picture such as MPGN, FPGN, FSGS and MCNS can be treated with addition of *Tinospora cordifolia* as an immuno-adjuvant. This enables safe long term use of steroid because of the ability of *Tinospora cordifolia* to counteract immune response, to reduce side effects of steroid therapy, to reduce relapse rate and infective episodes.

While the present invention has been described with reference to several particular implementations, those skilled in the art will recognize that many changes may be made hereto without departing from the spirit and scope of the present invention.

We claim:

1. A method for the treatment of a chronic recurrent urinary tract infection in a mammal in need thereof, the method comprising administering to the mammal a composition of a standardized extract of *Tinospora cordifolia* as an immuno-adjuvant in a dosage of 20 to 80 mg/kg body weight per day of the mammal, in conjunction with an antibacterial agent over a period ranging from 20 days to three months.

2. The method of claim 1, wherein the chronic recurrent urinary tract infection is both complicated and uncomplicated.

3. The method of claim 1, wherein the chronic recurrent urinary tract infection is caused due to relapsing bacterial infection.

4. The method of claim 3, wherein the relapsing bacterial infection is *E. coli* or Klebsiella infection.

5. The method of claim 1, wherein said composition comprising the standardized extract of *Tinospora cordifolia* is administered in a dosage of 20-25 mg/kg body weight over a period of one month.

6. The method of claim 1, wherein said antibacterial agent is selected from the group consisting of ciprofloxacin, ofloxacin, norfloxacin, trimethoprim, sulfamethoxazole, amoxicillin, nitrofurantoin, ampicillin and lomefloxacin.

* * * * *